(12) United States Patent
Fuke

(10) Patent No.: US 7,855,557 B2
(45) Date of Patent: Dec. 21, 2010

(54) GAS NUCLEAR MAGNETIC RESONANCE APPARATUS

(75) Inventor: Kiyokazu Fuke, Kobe (JP)

(73) Assignee: National University Corporation Kobe University, Kobe-shi (JP)

(*) Notice: Subject to any disclaimer, the term of this patent is extended or adjusted under 35 U.S.C. 154(b) by 330 days.

(21) Appl. No.: 12/161,068

(22) PCT Filed: Jan. 9, 2007

(86) PCT No.: PCT/JP2007/050102

§ 371 (c)(1),
(2), (4) Date: Jul. 16, 2008

(87) PCT Pub. No.: WO2007/080857

PCT Pub. Date: Jul. 19, 2007

(65) Prior Publication Data

US 2010/0156410 A1    Jun. 24, 2010

(30) Foreign Application Priority Data

Jan. 16, 2006 (JP) .............................. 2006-006887

(51) Int. Cl.
*G01V 3/00* (2006.01)
(52) U.S. Cl. ...................................... 324/307
(58) Field of Classification Search .......... 324/300–322
See application file for complete search history.

(56) References Cited

U.S. PATENT DOCUMENTS 4,315,149 A * 2/1982 Ledford, Jr. ................. 250/282

(Continued)

FOREIGN PATENT DOCUMENTS

JP    48 21069    6/1973

(Continued)

OTHER PUBLICATIONS

Rabi, I. I. et al., "The Molecular Beam Resonance Method for Measuring Nuclear Magnetic Moments", Physical Review, vol. 55, pp. 526-535, (1939).

*Primary Examiner*—Brij B Shrivastav
*Assistant Examiner*—Dixomara Vargas
(74) *Attorney, Agent, or Firm*—Oblon, Spivak, McClelland, Maier & Neustadt, L.L.P.

(57) ABSTRACT

An NMR apparatus is provided, which is capable of being used for mass spectrometry and structure determination of a gas sample. The NMR apparatus includes: a sample vaporization unit 1 having a sample vaporization chamber 1a; an ionization unit 2 having a ionization chamber 2a and connected to one end of the sample vaporization unit 1 so that the ionization chamber 2a communicates with the sample vaporization chamber 1a; a long-length pipe 3 connected to one end of the ionization unit 2 so that the inside of the pipe 3 communicates with the ionization chamber 2a; a cooling unit 4 having a cooling chamber 4a and connected to one end of the long-length pipe 3 so that the cooling chamber 4a communicates with the inside of the long-length pipe 3; a superconducting magnet 5 having a tubular portion 5a into which the long-length pipe 3 is inserted, the superconducting magnet 5 being capable of applying a magnetic field and a gradient magnetic field in the axial direction of the long-length pipe 3; an ion guide 6 which decelerates gas ions; a mass analysis unit 7 which is used for mass screening of gas ions; and a nuclear magnetic force amplification unit 8 which amplifies the nuclear magnetic force of gas ions.

7 Claims, 4 Drawing Sheets

U.S. PATENT DOCUMENTS

| | | | | |
|---|---|---|---|---|
| 4,686,365 A | * | 8/1987 | Meek et al. | 250/281 |
| 4,755,670 A | * | 7/1988 | Syka et al. | 250/292 |
| 4,761,545 A | * | 8/1988 | Marshall et al. | 250/291 |
| 4,855,593 A | * | 8/1989 | Bodenhausen et al. | 250/282 |
| 4,931,640 A | * | 6/1990 | Marshall et al. | 250/291 |
| 4,945,234 A | * | 7/1990 | Goodman et al. | 250/291 |
| 5,248,882 A | * | 9/1993 | Liang | 250/291 |
| 6,919,562 B1 | * | 7/2005 | Whitehouse et al. | 250/288 |
| 7,049,584 B1 | * | 5/2006 | Whitehouse et al. | 250/288 |
| 7,576,318 B2 | * | 8/2009 | Malek et al. | 250/282 |
| 2006/0125477 A1 | * | 6/2006 | Killoran et al. | 324/321 |

FOREIGN PATENT DOCUMENTS

| | | |
|---|---|---|
| JP | 2 118441 | 5/1990 |
| JP | 3 210463 | 9/1991 |
| JP | 6 331578 | 12/1994 |
| JP | 2005 172597 | 6/2005 |

* cited by examiner

FIG. 3
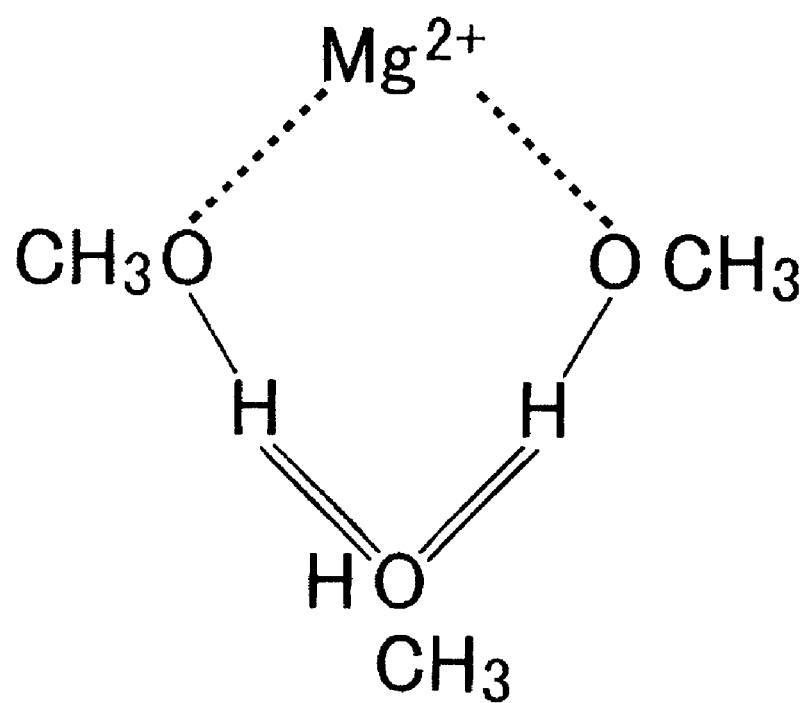

GAS NUCLEAR MAGNETIC RESONANCE APPARATUS

TECHNICAL FIELD

The present invention relates to a nuclear magnetic resonance (hereinafter referred to as "NMR") apparatus which is capable of being used for mass spectrometry and structure determination of a gas sample.

BACKGROUND ART

A conventional NMR apparatus has been widely used in research and development in the field of natural science, as one technique for analyzing and determining the structure of a liquid or solid sample (for example, see the below-described patent document 1).

Patent document 1: Japanese Unexamined Patent Publication No. 2005-172597

DISCLOSURE OF THE INVENTION

Problems to be Solved by the Invention

However, a sample measurable by such a conventional NMR apparatus is almost limited to a sample having a concentration of $10^{16}$ molecules/cm$^3$ or more, and therefore it has been difficult in principle to apply such an NMR apparatus to measurement of a gas ion sample.

Now, an object of the present invention is to provide an NMR apparatus which is capable of simultaneously performing mass spectrometry and structure determination of a gas sample.

Means for Solving the Problems and Effects

An NMR apparatus of the present invention includes: (i) an ionization unit which ionizes a sample gas to generate gas ions; (ii) a mass analysis unit having: an Ion Cyclotron Resonance (ICR) cell which has a tubular shape and conducts mass screening of the gas ions introduced from the ionization unit to the inside of the ICR cell; and a first pair of electrodes which are provided so as to sandwich the ICR cell in an axial direction and introduce the gas ions into the ICR cell, keep the gas ions in the ICR cell, or discharge the gas ions from the ICR cell, the mass analysis unit being provided in a high vacuum space to which a predetermined magnetic field is applied in the axial direction; and (iii) a nuclear magnetic force amplification unit having: a tubular cell provided in a portion to which a predetermined gradient magnetic field is applied in the axial direction within the high vacuum space to which the predetermined magnetic field is applied, into which tubular cell gas ions subjected to mass screening in the mass analysis unit are introduced; two pairs of RF coils provided so as to sandwich the tubular cell in the axial direction, the two pairs of RF coils being capable of applying an RF magnetic field perpendicularly to the axial direction of the tubular cell at both axial ends of the tubular cell; and a second pair of electrodes provided so as to sandwich, in the axial direction, a space to which the RF magnetic field is applied, the second pair of electrodes introducing the gas ions from the mass analysis unit to the tubular cell, keeping the gas ions, or discharging the gas ions, the nuclear magnetic force amplification unit amplifying nuclear magnetic forces of the gas ions. In the NMR apparatus, among the gas ions, only the gas ions corresponding to a predetermined nuclear magnetic resonance frequency are arranged to have amplified nuclear magnetic forces in the nuclear magnetic force amplification unit, and are reintroduced to the ICR cell, so that ion concentration and velocity increment are measured. Note that, in the present application, velocity increment is $\Delta V$ expressed by the following equation. In the following equation, N, v0, and M are the number of reciprocations of the ion packet, initial velocity, and ion mass, respectively. L and dB/dz are the effective length and gradient strength of the gradient magnetic field, respectively, and $\mu_z$ and $N_p$ are the magnetic moment and the number of protons having the same chemical environment in a molecular ion, respectively.

$$\Delta V = 2N(L/v_0)(1/M)\mu_z(dB/dz)N_p$$

According to the above structure, after subjected to the mass screening in the ICR cell, the gas ions are introduced into the tubular cell of the nuclear magnetic force amplification unit and perform a translational motion in the predetermined magnetic field and the predetermined gradient magnetic field. Among those gas ions, nuclear spins of the gas ions corresponding to the nuclear magnetic resonance frequency are reversed by the two pairs of RF coils disposed near the ends of the tubular cell, respectively. This makes it possible to reciprocate the gas ions in the axial direction in the tubular cell and accelerate (decelerate) the ions, with the result that magnetic heating and magnetic cooling of the gas ions is achievable. Among these gas ions, the gas ions corresponding to the predetermined nuclear magnetic resonance frequency are the only ones that their nuclear magnetic forces are amplified. Thereafter the gas ions whose nuclear magnetic forces have been amplified are then reintroduced into the ICR cell so that ion concentration and velocity increment are measured. The velocity increment is proportional to NMR absorption at each resonance frequency and corresponds to an NMR signal, which means that an NMR spectrum of the gas ions has been observed at the predetermined nuclear magnetic resonance frequency. Therefore, the measurement of velocity increment of gas ions of a sample for each desired nuclear magnetic resonance frequency makes it possible to observe an NMR spectrum for each nuclear magnetic resonance frequency. Accordingly, there can be provided an NMR apparatus which is capable of being used for analysis and structure determination of a gas sample.

It is preferable that the NMR apparatus of the present invention includes: a third pair of electrodes which sandwich the second pair of electrodes in the axial direction of the tubular cell; and gas ion injection controlling means electrically connected to the third pair of electrodes, the gas ion injection controlling means performing control so as to improve ion packet density by injecting, in the same phase as amplification motion of the gas ions in the nuclear magnetic force amplification unit, gas ions which are present in the ICR cell into the tubular cell in a pulsed manner.

With this structure, the width of the ion packet injected from the ICR cell to the nuclear magnetic force amplification unit is narrowed so that the ion packet is pulsed, and the ion packet can be injected in the same phase as amplification motion of the gas ions. Because of this, ion packet density is improved in the nuclear magnetic force amplification unit. As a result, it is possible to enhance the amplification effect of nuclear magnetic force in the nuclear magnetic force amplification unit, thereby improving sensitivity.

It is preferable that the NMR apparatus of the present invention further includes a refrigerator which cools the inside of a long-length pipe, with the result that the gas ions are cooled while being trapped in the ICR cell, before the gas ions are introduced into the nuclear magnetic force amplification unit. This enhances the amplification effect of nuclear magnetic force of gas ions in the nuclear magnetic force amplification unit, thereby further improving sensitivity.

BEST MODE FOR CARRYING OUT THE INVENTION

The following describes an NMR apparatus according to an embodiment of the present invention. FIG. 1 is a schematic diagram illustrating a main part of the NMR apparatus according to an embodiment of the present invention. FIG. 2 is a perspective view illustrating a mass analysis unit and a nuclear magnetic force amplification unit of the NMR apparatus of FIG. 1. Note that, in FIG. 1, the mass analysis unit and the nuclear magnetic force amplification unit are illustrated in a simplified manner, as a matter of convenience.

As shown in FIG. 1, an NMR apparatus 10 includes: a sample vaporization unit 1 having a sample vaporization chamber 1$a$; an ionization unit 2 having a ionization chamber 2$a$ and connected to one end of the sample vaporization unit 1 so that the ionization chamber 2$a$ communicates with the sample vaporization chamber 1$a$; a long-length pipe 3 connected to one end of the ionization unit 2 so that the inside of the pipe 3 communicates with the ionization chamber 2$a$; a cooling unit 4 having a cooling chamber 4$a$ and connected to one end of the long-length pipe 3 so that the cooling chamber 4$a$ communicates with the inside of the long-length pipe 3; a superconducting magnet 5 having a tubular portion 5$a$ into which the long-length pipe 3 is inserted, the superconducting magnet 5 being capable of applying a magnetic field and a gradient magnetic field in the axial direction of the long-length pipe 3; an ion guide 6 which decelerates gas ions; a mass analysis unit 7 which is used for mass screening of gas ions; and a nuclear magnetic force amplification unit 8 which amplifies nuclear magnetic force of gas ions. In addition, pumps (not shown) are connected to tubes that are in communication with the sample vaporization chamber 1$a$, the ionization chamber 2$a$, and the cooling chamber 4$a$, respectively, so that high vacuum can be achieved in the whole internal spaces communicating with each other.

The sample vaporization unit 1 is a unit in which a liquid sample or a solid sample is vaporized in the sample vaporization chamber 1$a$, and the thus vaporized sample is introduced into the ionization unit 2. Liquid is vaporized by means of heating. A solid is vaporized by means of irradiation of a laser for vaporization. However, each vaporization method is not limited thereto, and other methods may be employed.

The ionization unit 2 is a unit in which the vaporized sample introduced from the sample vaporization chamber 1$a$ is ionized in the ionization chamber 2$a$. Electron ionization, chemical ionization, or the like can be used for ionization depending on the state of a sample, but not limited thereto.

Meanwhile, when a method of performing vaporization and ionization simultaneously or almost simultaneously (for example, desorption electron ionization, desorption chemical ionization, fast atom bombardment, electrospray ionization, or the like) is selected, the sample vaporization unit 1 and the ionization unit 2 may be combined together into one unit. In addition, when the sample is gas in the first place, an NMR apparatus 10 without the sample vaporization unit 1 may be used.

The long-length pipe 3, which is inserted into the tubular portion 5$a$ of the superconducting magnet 5, is configured so that the magnetic field generated by the superconducting magnet is applied to the almost entirety of the pipe 3 and a gradient magnetic field is further applied to a predetermined portion of the pipe 3. Inside the long-length pipe 3, the ion guide 6, the mass analysis unit 7, and the nuclear magnetic force amplification unit 8 are disposed in this order so as to align along the direction from the ionization unit 2 to the cooling unit 4.

The superconducting magnet 5 includes: a cryostat 5$b$ which is a low-temperature container having the tubular portion 5$a$; a main magnetic field generating coil (not shown) which is provided in the cryostat 5$b$ and implements a uniform magnetic field region in the axial direction in the tubular portion 5$a$; and a gradient magnetic field generating coil (not shown) which generates a gradient magnetic field in the axial direction in a predetermined portion of the tubular portion 5$a$ (i.e. all over the nuclear magnetic force amplification unit 8 of FIG. 1), by changing an electric current value. The main magnetic field generating coil is a wounded superconducting coil connected to a power source, and is cooled to about a superconductive transition temperature or less by a cooling device (not shown) provided in the cryostat 5$b$ or by a contact with, for example, liquid helium in a liquid helium bath (not shown). The gradient magnetic field generating coil may be realized by a superconducting coil or by a normal-conducting coil. When the gradient magnetic field generating coil is realized by a superconducting coil, it is necessary to cool the superconducting coil to about a superconductive transition temperature or less, as is in the case with the main magnetic field generating coil.

To the ion guide 6, a pulse voltage can be applied to take away translational energy of gas ions. The application of the voltage decelerates the gas ions to 1 eV or less, thereby improving trapping efficiency of gas ions in the mass analysis unit 7.

The mass analysis unit 7 includes: a pair of mesh-like electrodes 7$a_1$, 7$a_2$ (a first pair of electrodes); and an ICR cell 7$b$ interposed between the electrodes 7$a_1$ and 7$a_2$ in the axial direction of the long-length pipe 3 (between (A)-(B) of FIG. 2). The ICR cell 7$b$ is a quadrangular tube shape cell constituted of four plate-like electrodes 7$b_1$, 7$b_2$, 7$b_3$, and 7$b_4$. When the opposed electrodes 7$b_1$ and 7$b_4$ are used as excitation electrodes, the other opposed electrodes 7$b_2$ and 7$b_3$ are used as detection electrodes. To the contrary, when the opposed electrodes 7$b_1$ and 7$b_4$ are used as detection electrodes, the other opposed electrodes 7$b_2$ and 7$b_3$ are used as excitation electrodes. The present embodiment assumes that the electrodes 7$b_1$ and 7$b_4$ are excitation electrodes, and the electrodes 7$b_2$ and 7$b_3$ are detection electrodes.

The nuclear magnetic force amplification unit 8 has: mesh-like electrodes 8$a_1$ and 8$a_2$ (a third pair of electrodes); mesh-like electrodes 8$b_1$ and 8$b_2$ (a second pair of electrodes); a pair of RF coils 8$c_1$, 8$c_2$; a pair of RF coils 8$c_3$, 8$c_4$; and a quadrangular tube shape cell 8$d$. As shown in (C) to (F) of FIG. 2, these members are arranged in the direction from the mass analysis unit 7 to the cooling unit 4 in the following order: electrode 8$a_1$; electrode 8$b_1$; the pair of RF coils 8$c_1$, 8$c_2$; the quadrangular tube shape cell 8$d$; the pair of RF coils 8$c_3$, 8$c_4$; the electrode 8$b_2$; and the electrode 8$a_2$. The pair of RF coils 8$c_1$, 8$c_2$, and the pair of RF coils 8$c_3$, 8$c_4$ are placed near the respective ends of the cell 8$d$ and disposed so as to interpose a passage area of gas ions but not to block the passage area, and these pairs of coils are configured to be capable of applying an RF magnetic field perpendicularly to the axial direction of the cell 8$d$. The cell 8$d$ is a quadrangular tube shape cell formed of four plate-like members 8$d_1$, 8$d_2$, 8$d_3$, and 8$d_4$. Note that, only either pair of members, the opposed plate-like members 8$d_1$ and 8$d_4$ or the opposed plate-like members 8$d_2$ and 8$d_3$, is required to be a pair of electrodes.

The cooling unit 4 includes: the cooling chamber 4$a$; a refrigerator 4$b$ inserted from the top while the cooling chamber 4a is sealed; and a heat transfer member 4c which cools the ICR cell 7b. This arrangement cools gas ions, thereby enhancing the amplification effect of nuclear magnetic force of gas ions in the nuclear magnetic force amplification unit 8, resulting in further improvement in sensitivity.

Next, described is an operation of the NMR apparatus 10. First, the not-shown pumps are operated to cause the sample vaporization chamber 1a, the ionization chamber 2a, the inside of the long-length pipe 3, and the cooling chamber 4a, which are located in the NMR apparatus 10, to be in high vacuum. Also, the superconducting magnet 5 is energized to apply a predetermined uniform magnetic field to the inside of the long-length pipe 3 and to apply a gradient magnetic field to the cell 8d (between (D) and (E) of FIG. 2). Next, in the sample vaporization chamber 1a of the sample vaporization unit 1, a liquid sample or a solid sample is vaporized by means of a heater, a laser, or the like. Then, the vaporized sample is introduced into the ionization chamber 2a of the ionization unit 2, by injection or the like, and then the sample is ionized using electron ionization before being introduced into the long-length pipe 3, so that gas ions are generated. When introduced into the long-length pipe 3, the generated gas ions undergo cyclotron motion in the uniform magnetic field caused by the superconducting magnet 5. Then, the gas ions are, while undergoing cyclotron motion, introduced into the ion guide 6 in the long-length pipe 3, having a pulse voltage applied thereto. The gas ions are decelerated to 1 eV or less after leaving the ion guide 6 and before reaching the electrode $7a_1$ of the mass analysis unit 7. Then, the decelerated gas ions are introduced into and trapped in the ICR cell 7b provided between the electrodes $7a_1$ and $7a_2$ each having a voltage applied thereto. Among the gas ions decelerated via the ion guide 6, only the gas ions that have got over the voltage at the electrode $7a_1$ are able to enter into the ICR cell 7b.

In the ICR cell 7b, a varying electric field is applied to the electrodes $7b_1$ and $7b_4$, which are excitation electrodes, thereby exciting gas ions and increasing the radius of rotational motion of the cyclotron motion. This causes gas ions to be close to the electrodes $7b_2$ and $7b_3$, which are detection electrodes, so that induced current is efficiently generated between the electrodes $7b_2$ and $7b_3$. At this time, the induced current flowing between the electrodes $7b_2$ and $7b_3$, which are detection electrodes, is taken and converted to voltage. This voltage is amplified through an amplifier (not shown), and observed in the form of a sine wave using electronic test equipment (not shown) such as an oscilloscope. From the data observed in the form of a sine wave whose abscissa axis represents time, a spectrum whose abscissa axis represents frequency f is obtained by Fourier transformation. After the Fourier transformation, by means of expression $m/z = B/2\pi f$ (m: gas ion mass, z: valence of gas ion, B: magnetic flux density, f: frequency of circular motion of gas ion), the abscissa axis of the obtained frequency spectrum is converted to mass-to-charge ratio m/z, so that a mass spectrum is obtained. In the ICR cell 7b, a varying electric field having a frequency other than the frequency to excite target gas ions is applied to the electrodes $7b_1$ and $7b_4$ which are excitation electrodes. This makes it possible to remove, from the ICR cell 7b, excited gas ions which are not the target gas ions (mass screening). The target gas ions remaining in the ICR cell 7b are introduced into the nuclear magnetic force amplification unit 8 by decreasing the voltages at the electrode $7a_2$ and the electrodes $8a_1$ and $8b_1$. Meanwhile, the gas ions are cooled by the refrigerator 4b to about 10 K before they pass through the ICR cell 7b.

Next, a voltage is applied to the electrodes $8a_1$ and $8a_2$ to narrow the width of gas ion packet passed through the ICR cell 7b (so that the ion packet is pulsed). Then, the gas ions are introduced into the cell 8d provided between the electrodes $8a_1$ and $8a_2$ each having a voltage applied thereto (voltages are applied so that the voltage between $8d_1$ and $8d_3$, and the voltage between $8d_2$ and $8d_4$ are 0 V, for example, $8d_1 = -1$ V, $8d_2 = 8d_3 = 1$ V, $8d_4 = -1$ V). In the meantime, the electrode $8a_1$ is used for screening the speed of gas ions. Therefore a pulse electric field is applied to the electrode 8a in order to set the speed distribution so that the ion packet falls within an active region of the below-mentioned RF magnetic field. At this time, using a gas ion injection controlling apparatus (not shown), a new gas ion packet is injected in a pulsed manner from the mass analysis unit 7 to the cell 8d so as to overlap with the motion of the already presented ion packet at the same phase, so that the density of ion packet of gas ions is improved. As a result, it is possible to improve ion concentration in the nuclear magnetic force amplification unit 8, thereby improving sensitivity.

Here, the above-described gas ion injection controlling apparatus will be described. The gas ion injection controlling apparatus is constituted by a computer having a predetermined program, and is electrically connected to a predetermined part of the NMR apparatus 10 so as to be capable of outputting a command thereto. The gas ion injection controlling apparatus is therefore capable of performing the following operations. First, output and ordered to be executed is a command to decrease the potential of electrode $7a_2$ thereby releasing the gas ions cooled in the ICR cell 7b toward the nuclear magnetic force amplification unit 8 (process 1). Then, output and ordered to be executed is a command to set the voltage at the electrode $8b_1$ to 0 V while decreasing the voltage at the electrode $8a_1$ from the initial set value of 1 V to 0 V only during a time interval of about 10 microseconds, thereby introducing gas ions into the cell 8d to form an ion packet. Each of the gas ions has a initial velocity ($v_0$) of a most probable velocity determined in accordance with a cooling temperature. That initial velocity $v_0$ is a known value which has been measured in advance. With reference to the time at which the electrode $8a_1$ and $8b_1$ start to create an acceptance state (start time: $T_0$), the position and time of the ion packet are computed based on the flight distance and flight time of the ion packet performing simple harmonic motion (process 2). When the number density in the ion packet is doubled by outputting a command to reintroduce gas ions and causing the NMR apparatus 10 to execute the command, the period of time of one reciprocation of the ion packet previously introduced is determined from $v_0$ and the length of the cell 8d, and the processes 1 and 2 are repeated. The introduced ion packet repeatedly performs simple harmonic motion in the cell 8d for a long time. As described above, the time at which ion packet reaches an end of the cell 8d can be easily determined from $v_0$, and the timing at which an RF magnetic field is applied to reverse spins is controlled by the computer. These timings are contemplated in detail in advance through a preliminary experiment. Specifically, after the gas ions are introduced and reciprocated a predetermined number of times, the gas ions are transferred to the ICR cell 7b by decreasing the potential of the electrodes $8a_1$ and $8b_1$, so that the number of ions is measured, and a calibration curve or the like is produced. With this, data about basic characteristics in the cell 8d is stored in a memory device in the computer of the gas ion injection controlling apparatus. Based on this data, measurement is performed under the control of the computer of the gas ion injection controlling apparatus.

Next, when the gas ions reach the tail end of the cell 8d, a voltage is applied to the pair of RF coils $8c_1$, $8c_2$, and the pair of RF coils $8c_3$, $8c_4$ successively in synchronization with each other, so that an RF magnetic field is applied in a direction perpendicular to the axial direction of the cell $8d$. Under this circumstance, nuclear spin of each gas ion is reversed by the RF magnetic field at both ends of the cell $8d$. Accordingly, the gas ions are gradually accelerated while reciprocating in the cell $8d$ in the axial direction and nuclear magnetic force becomes amplified. After such amplification is performed several times or more, application of the RF magnetic field to the pair of RF coils $8c_1$, $8c_2$ is stopped, and the voltages at the electrodes $8a_1$ and $8b_1$ are decreased to predetermined values. As a result, among the gas ions, only the gas ions each having a predetermined kinetic energy or more or having a predetermined speed or higher due to the amplification of the nuclear magnetic force are reintroduced into the ICR cell $7b$ of the mass analysis unit 7. In other words, only the ions that have absorbed the RF magnetic field with a specific frequency are accelerated, while the ions that keep an initial velocity or less are subjected to a repulsive voltage. Therefore, the accelerated ions get over and pass through the gate of $8b_1$ and $8a_1$, and are trapped in the ICR cell $7b$. In the ICR cell $7b$, ion concentration of the reintroduced gas ions is observed. Since all these ions satisfy a nuclear magnetic resonance condition and have absorbed RF waves, a relation between the velocity increment calculated from the kinetic energy determined by the voltage applied to the $8a_1$ and the RF frequency corresponds to an NMR spectrum. This means that an NMR spectrum is observed. Meanwhile, in the case of different frequency and no absorption, ions are not accelerated, and therefore no gas ion reaches the ICR cell $7b$. In addition, reciprocation performed about ten times in the cell $8d$ results in ion concentration of about 2000 ions.

Note that, the above-mentioned velocity increment can be alternatively obtained in such a way that the time to reach the electrode $8a_1$ is determined by variously varying the time during which ions are introduced into the ICR cell $7b$ by decreasing the voltage applied to the electrode $8a_1$.

Accordingly, an NMR spectrum corresponding to each nuclear magnetic resonance frequency can be obtained by: performing the above-described operations for sample gas ions at a desired nuclear magnetic resonance frequency w; counting the number of ions (N) trapped in the ICR cell $7b$ for each nuclear magnetic resonance frequency ω and obtaining velocity increment at the same time; and two-dimensionally plotting the relation between ω and ΔV. This can be helpful for structure determination of the gas sample. Note that, three-dimensional plot is also possible, by setting the number of ions as a coordinate of the third dimension.

According to this embodiment, there can be provided the NMR apparatus 10 which has the above-described functions and effects and is utilizable for mass spectrometry and structure determination of a gas sample.

EXAMPLE

Next, the present invention will be described with reference to an Example. In this Example, a simulation of NMR spectrum was performed for $Mg^{2+}(CH_3OH)_3$ ($Mg^{2+}$-methanol cluster: see FIG. 3), using an apparatus similar to the NMR apparatus 10 of the above embodiment, under the following conditions.

In this Example, as a proton resonance frequency in a cluster, employed was a literature value of $Mg^{2+}$ in methanol solution (measured with a 60 MHz NMR apparatus) (see S. Nakamura and S. Meiboom, "Proton Magnetic Resonance Studies of the Solvation Shell of $Mg^{2+}$ in Methanol, J. American Chemical Society, 89, 1765 (1967)). Under the following simulation conditions, measured values (velocity increment $\Delta V=2N(L/v_0)(1/M)\mu_z(dB/dz)N_p)$ were obtained through calculation, and are plotted in comparison with the resonance frequencies on the graph shown in FIG. 4. Meanwhile, the abscissa axis and the ordinate axis in the plane of the graph of FIG. 4 respectively represent the resonance frequency (ppm) and the velocity increment ΔV. An axis perpendicular to the plane represents the number of ions, for illustration in the form of a contour plot. In addition, "83 MHz" in FIG. 4 represents a reference resonance frequency of protons in a magnetic field of 2T, which is the low magnetic field of the NMR apparatus of this simulation.

(Software used for the Simulation)

Simion 3D (Ver 7.0: produced by Idaho National Engineering and Environmental Laboratory)

(Simulation Conditions)

Ion mass (m/z): 60

High magnetic field: 12 T, low magnetic field: 2 T, gradient strength (dB/dz): 50 T/m, effective length of gradient magnetic field (L): 0.25 m Length of NMR cell: 0.5 m Initial velocity of translation of ion ($v_0$): 50 m/s Number of times ions reciprocate in cell (N): 20 times RF magnetic field area: 0.025 m×0.025 m, RF magnetic field strength: 0.02 G (gauss)

Spectrum resolution: 1 ppm

In the above-described simulation, ΔV is proportional to the number of protons (Np) having the same chemical environment in the cluster. There are three types of protons, each type having a different environment: (1) two O—H protons of methanol to be directly coordinated to a metal ion; (2) one O—H proton hydrogen bonded to coordinated methanol; and (3) nine $CH_3$ protons. As shown in the graph of FIG. 4, three resonance peaks of these types of protons were obtained. Therefore, this Example proved in simulation that use of a similar apparatus to the NMR apparatus 10 of the above embodiment provides three resonance peaks of the sample gas.

Note that various design variations can be made in the present invention without departing from the scope of the claims, and the present invention is not limited to the above-described embodiment or Example. For example, the cell $8d$ of the above embodiment is a quadrangular tube shape cell with four plate-like electrodes. However, instead of this quadrangular tube shape cell, there may be used a cell with four plate-like electrodes each having a curved face, which electrodes are assembled to form a substantially cylindrical shape as a whole.

Although not shown, ions may be counted in the following manner: an ion detector having a center hole (e.g., a photosensor such as a ring-shape microchannel plate) is mounted in the ionization chamber $2a$ of the above embodiment so that the detection surface thereof faces to the ICR cell $7b$; and ions are accelerated in the above-described nuclear magnetic force amplification unit 8, then reintroduced into the ICR cell $7b$, and guided into the ion detector through the ion guide 6. This can improve ion detection sensitivity, compared to the case where detection is performed by only the ICR cell $7b$.

BRIEF DESCRIPTION OF THE DRAWINGS

FIG. 3 A diagram showing the structural formula of a sample used in an Example of the present invention.

REFERENCE NUMERALS

Figure 1:
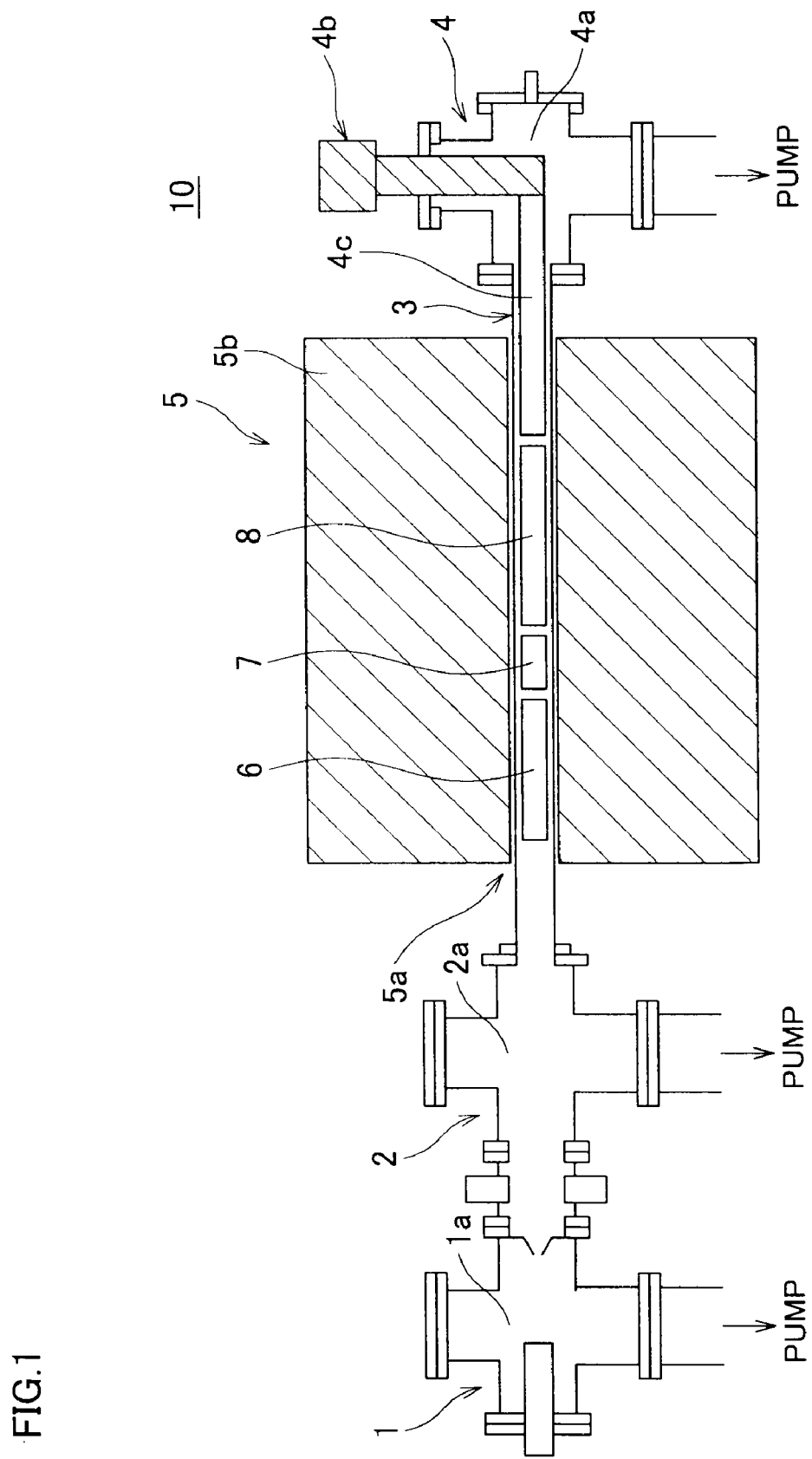
FIG. 1 is a schematic diagram illustrating a main part of an NMR apparatus according to an embodiment of the present invention.
Figure 2:
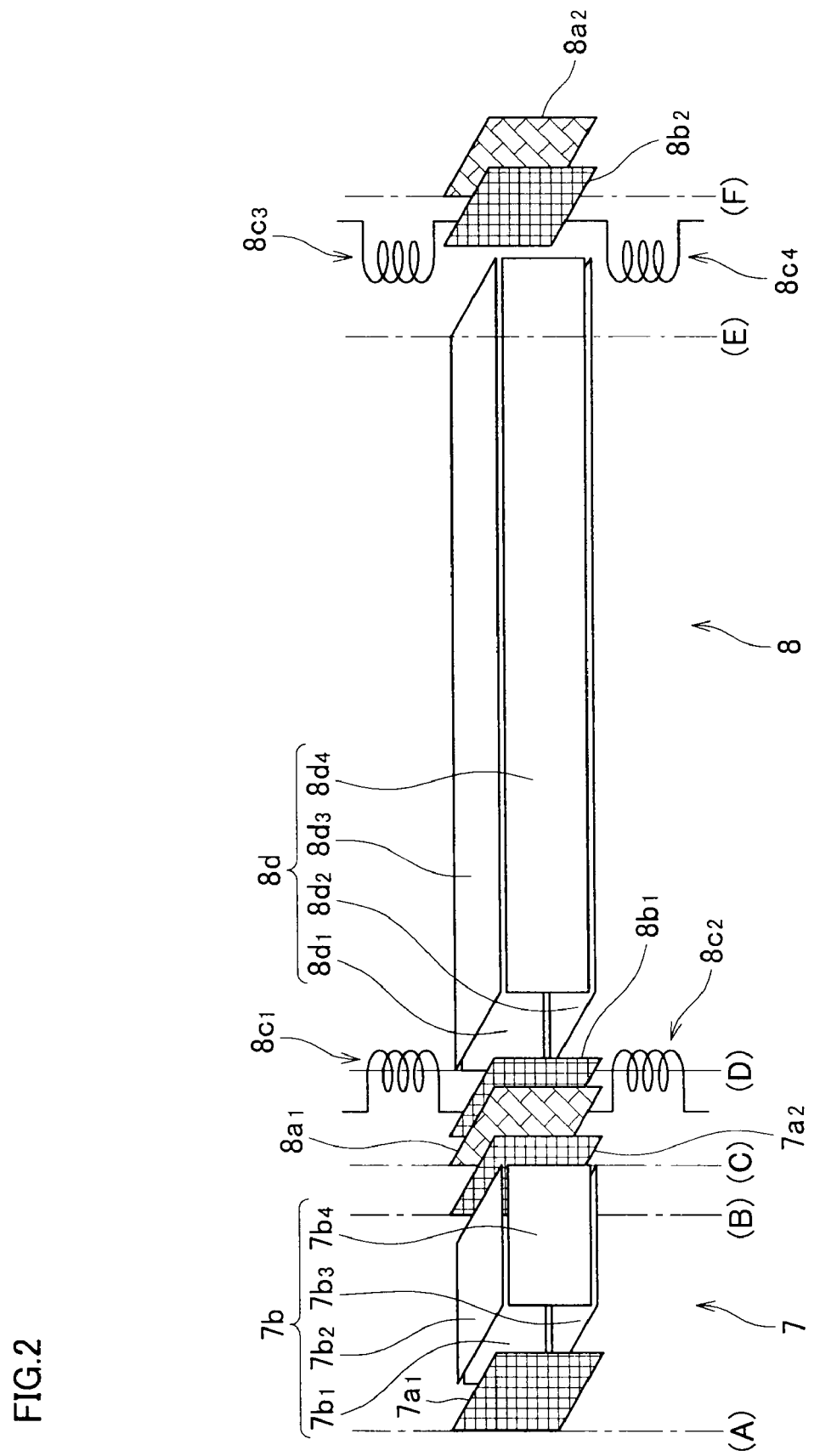
FIG. 2 A perspective view illustrating a mass analysis unit and a nuclear magnetic force amplification unit of the NMR apparatus of FIG. 1.
Figure 4:
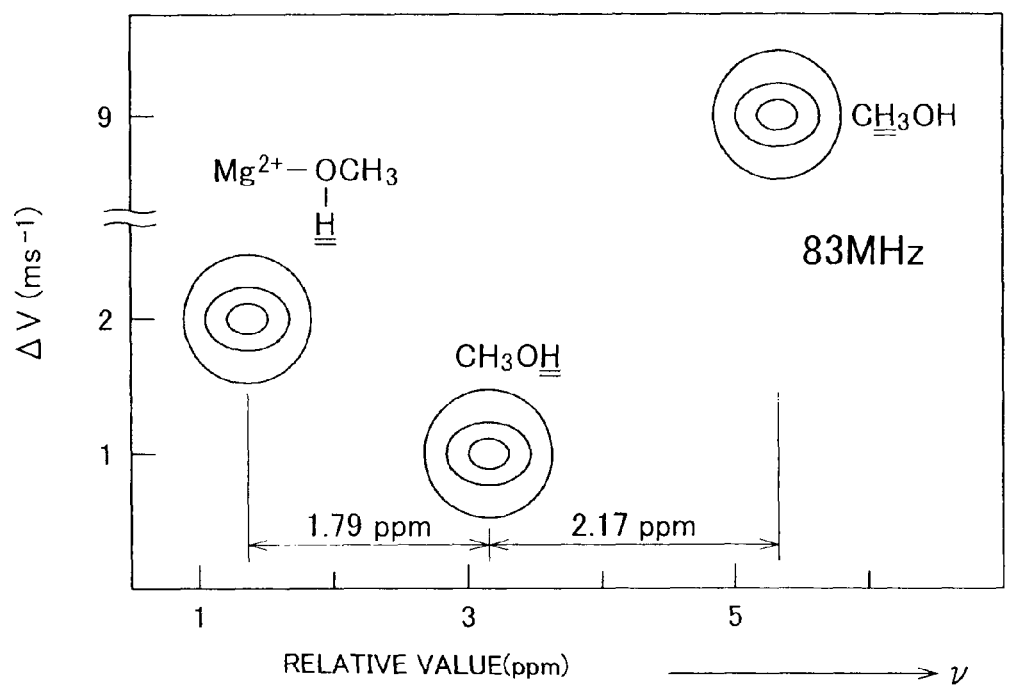
FIG. 4 A graph showing the results obtained in the Example of the present invention.

1 Sample vaporization unit
1a Sample vaporization chamber
2 Ionization unit
2a Ionization chamber
3 Long-length pipe
4 Cooling unit
4a Cooling chamber
4b Refrigerator
4c Heat transfer member
5 Superconducting magnet
5a Tubular portion
5b Cryostat
6 Ion guide
7 mass analysis unit
$7a_1, 7a_2, 7b_1, 7b_2, 8a_1, 8a_2, 8b_1, 8b_2$ Electrode
7b ICR cell
8 Nuclear magnetic force amplification unit
$8c_1, 8c_2$ Pair of coils
$8c_3, 8c_4$ Pair of coils
8d Cell
$8d_1, 8d_2, 8d_3, 8d_4$ Plate-like member
10 NMR apparatus

The invention claimed is:

1. A gas nuclear magnetic resonance apparatus comprising:
a mass analysis unit including: an ICR cell disposed in a high vacuum space to which a predetermined magnetic field is applied in a predetermined direction, the ICR cell conducting mass screening of introduced gas ions; and a first gas ion controller which introduces the gas ions into the ICR cell, keeps the gas ions in the ICR cell, or discharges the gas ions from the ICR cell; and
a nuclear magnetic force amplification unit located within said gas nuclear magnetic resonance apparatus including: a nuclear magnetic force amplification cell disposed in a high vacuum space to which a predetermined gradient magnetic field is applied in the predetermined direction, into which cell gas ions subjected to mass screening in the mass analysis unit are introduced; an amplification unit which amplifies, in the nuclear magnetic force amplification cell, nuclear magnetic forces only of gas ions having a predetermined nuclear magnetic resonance frequency; and a second gas ion controller which introduces the gas ions into the nuclear magnetic force amplification cell, keeps the gas ions in the nuclear magnetic force amplification cell, or discharges the gas ions from the nuclear magnetic force amplification cell,
wherein the gas ions having the predetermined nuclear magnetic resonance frequency, which have been amplified in the nuclear magnetic force amplification unit, are reintroduced into the ICR cell.

2. The gas nuclear magnetic resonance apparatus according to claim 1, wherein the amplification unit is provided at respective ends of the nuclear magnetic force amplification cell in the predetermined direction, and includes two pairs of RF coils each configured to apply an RF magnetic field perpendicularly to the predetermined direction.

3. The gas nuclear magnetic resonance apparatus according to claim 2,
wherein the first gas ion controller includes a first pair of electrodes provided at respective ends of the ICR cell in the predetermined direction, and
the second gas ion controller includes a second pair of electrodes respectively disposed, in the predetermined direction, outside spaces to which the pairs of RF coils apply the RF magnetic fields.

4. The gas nuclear magnetic resonance apparatus according to claim 1, further comprising a magnetic field generating unit which applies uniform magnetic fields having intensities different from one another to respective end portions of the high vacuum space in the predetermined direction, and generates, between the respective end portions to which the uniform magnetic fields are applied, a gradient magnetic field whose magnetic field intensity varies,
wherein the ICR cell is disposed at a portion to which one of the uniform magnetic fields serving as the predetermined magnetic field is applied, and the nuclear magnetic force amplification cell is disposed at a portion to which the gradient magnetic field is applied.

5. A gas nuclear magnetic resonance apparatus comprising:
an ionization unit which ionizes a sample gas to generate gas ions;
a mass analysis unit including: an ICR cell which has a tubular shape and conducts mass screening of the gas ions introduced from the ionization unit to the inside of the ICR cell; and a first pair of electrodes which are provided so as to sandwich the ICR cell in an axial direction and introduce the gas ions into the ICR cell, keep the gas ions in the ICR cell, or discharge the gas ions from the ICR cell, the mass analysis unit being provided in a high vacuum space to which a predetermined magnetic field is applied in the axial direction; and
a nuclear magnetic force amplification unit located within said gas nuclear magnetic resonance apparatus including: a tubular cell provided in a portion to which a predetermined gradient magnetic field is applied in the axial direction within the high vacuum space to which the predetermined magnetic field is applied, into which tubular cell gas ions subjected to mass screening in the mass analysis unit are introduced; two pairs of RF coils provided so as to sandwich the tubular cell in the axial direction, the two pairs of RF coils being capable of applying an RF magnetic field perpendicularly to the axial direction of the tubular cell at both axial ends of the tubular cell; and a second pair of electrodes provided so as to sandwich, in the axial direction, a space to which the RF magnetic field is applied, the second pair of electrodes introducing the gas ions from the mass analysis unit to the tubular cell, keeping the gas ions in the tubular cell, or discharging the gas ions from the tubular cell, the nuclear magnetic force amplification unit amplifying nuclear magnetic forces of the gas ions,
wherein, among the gas ions, only the gas ions corresponding to a predetermined nuclear magnetic resonance frequency are arranged to have nuclear magnetic forces amplified by the pairs of RF coils in the nuclear magnetic force amplification unit, and are reintroduced to the ICR cell, so that ion concentration and velocity increment are measured.

6. The gas nuclear magnetic resonance apparatus according to claim 5, further comprising:
a third pair of electrodes which sandwich the second pair of electrodes in the axial direction of the tubular cell; and gas ion injection controlling means electrically connected to the third pair of electrodes, the gas ion injection controlling means performing control so as to improve ion packet density by injecting gas ions which are present in the ICR cell into the tubular cell in a pulsed manner in a same phase as amplification motion of the gas ions in the nuclear magnetic force amplification unit.

7. The gas nuclear magnetic resonance apparatus according to claim 5, further comprising a refrigerator which cools the inside of a long-length pipe, wherein the gas ions are cooled while being trapped in the ICR cell, before introduced into the nuclear magnetic force amplification unit.

* * * * *